(12) United States Patent
Johnson et al.

(10) Patent No.: US 7,045,309 B2
(45) Date of Patent: May 16, 2006

(54) 9-SUBSTITUTED ADENINE DERIVATIVES AS PRODRUG REGULATORS OF CELL AND TISSUE FUNCTION

(75) Inventors: Roger A. Johnson, East Setauket, NY (US); Praveen Pande, Coram, NY (US); Wolfgang Laux, Frankfurt (DE); Gilles Gosselin, Montpellier (FR)

(73) Assignee: The Research Foundation of State University of New York, New York, NY (US)

(*) Notice: Subject to any disclaimer, the term of this patent is extended or adjusted under 35 U.S.C. 154(b) by 139 days.

(21) Appl. No.: 10/332,314

(22) PCT Filed: Jul. 6, 2001

(86) PCT No.: PCT/US01/21523
§ 371 (c)(1),
(2), (4) Date: Jan. 7, 2003

(87) PCT Pub. No.: WO02/04475
PCT Pub. Date: Jan. 17, 2002

(65) Prior Publication Data
US 2004/0053825 A1 Mar. 18, 2004

Related U.S. Application Data
(60) Provisional application No. 60/216,869, filed on Jul. 7, 2000.

(51) Int. Cl.
*G01N 33/53* (2006.01)
*C07H 19/20* (2006.01)

(52) U.S. Cl. ............... 435/7.92; 436/86; 436/504; 436/545; 436/546; 436/547; 514/45; 514/47; 514/48; 536/26.5; 536/26.7; 544/264

(58) Field of Classification Search ............ 435/7.92, 435/183; 436/86, 504, 545–546, 547; 514/45, 514/47–48; 536/26.5, 26.7; 544/264
See application file for complete search history.

(56) References Cited

U.S. PATENT DOCUMENTS 3,910,885 A * 10/1975 Moffatt et al. ............ 536/27.13
5,449,664 A * 9/1995 Verheyden et al. .......... 514/45
5,795,756 A * 8/1998 Johnson et al. ............. 435/183

FOREIGN PATENT DOCUMENTS

WO    W O 02/04475 A1 * 1/2002

OTHER PUBLICATIONS

R. A. Johnson et al. (II), "Cation and Structural Requirements for P Site–Mediated Inhibition of Adenylate Cyclase," *Molecular Pharmacology*, 35, 681–688 (1989).*
Désaubry et al. (I), "Synthesis of 2'–Deoxy– and 2', 5'–Dideoxy–Adenosine–3'–Di– and 3'–Triphosphate," *Tetrahedron Letters*, 36(7), 995–996 (1995).*

R. A. Johnson et al. (III), "Adenylyl Cyclase 'P'–Site Inhibitors Induce Differentiation in ob–1771 Pre–Adipocytes," Abstract, XII Intl. Congress of Pharmacology, Montreal, Canada, Jul. 24–27, 1994, *Canadian J. Physiology Pharmacology*, 72(Suppl. 1), 511 (1994).*
Nakajima et al., "Facile and Selective Synthesis of Diadenosine Polyphosphates Through Catalysis of Leucyl–t–RNA Synthetase Coupled with ATP Regeneration," *Agricultural & Biological Chemistry*, 53(3), 615–623 (1989); *Chem. Abstracts*, 111(21), p. 408, Abstr. No. 190876w (Nov. 20, 1989).*
Cullis et al., "The Reactivity of Adenosine 5'–O–(S–methyl–1–thiotriphosphate): A Facile Way of Generating cyclo–Diphosphate Dianion," *J. Chem. Soc.: Chem. Communications*, Issue No. 2, 106–108 (Jan. 1989).*

(Continued)

Primary Examiner—James O. Wilson
Assistant Examiner—L. E. Crane
(74) Attorney, Agent, or Firm—Darby & Darby

(57) ABSTRACT

The present invention relates to 9-substituted adenine derivatives represented by formula (I)

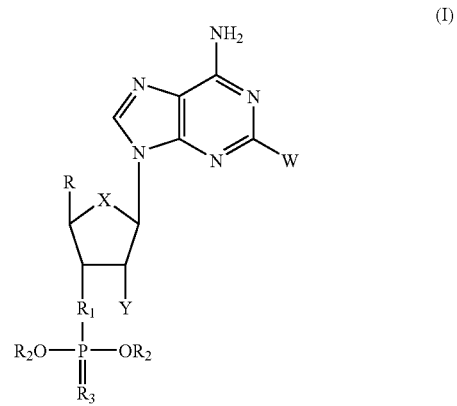

(I)

wherein W is selected from the group consisting of H, halogen, azido and amino group; X is selected from the group consisting of O, S, N(H), $CH_2$, CH and C; Y is selected from the group consisting of H, hydroxy, $C_{1-4}$ alkyl, $C_{1-4}$ alkoxy and halogen; R is selected from the group consisting of H, hydroxymethyl, $C_{1-4}$ alkyl, and $C_{1-4}$ alkoxy; $R_1$ is selected from the group consisting of O, NH and $CH_2$; $R_2$ represents a radical selected from the group consisting of —$(CH_2)_n$—S—C(O)—$R_4$ and —$(CH_2)_n$—S—S—$R_4$, where n=1–4 and $R_4$ is a $C_{1-4}$-alkyl or aryl group and $R_4$ is optionally substituted with a halogen, amino, N-alkylamino, N, N-dialkylamino or $C_{1-4}$ alkoxy group and wherein each of the $R_2$ radicals may be the same or different; and $R_3$ is O or S. The derivatives are useful as prodrugs for inhibiting adenylyl cyclase and lowering 3':5'-cAMP in cells, thereby inhibiting adenylyl cyclase dependent effects within cells.

20 Claims, No Drawings

OTHER PUBLICATIONS

Jankowska et al., "Chemical Synthesis of 5'–Phosphorylated DNA Fragments and Their Constituents," *Bulletin of the Polish Academy of Sciences, 31*(1–2), 17–22 (Oct., 1983); *Chem. Abstracts, 101*(1), pp. 654–655, Abstr. No. 7588k (Jul. 2, 1984).*

Kozarich et al., "Ribonucleoside 3'–Di– and –Triphosphates. Synthesis of Guanosine Tetraphosphate (ppGpp)," *Biochemistry, 14*(5), 981–988 (Mar. 11, 1975).*

Etaix et al., "Phosphorylation of Nucleosides in Aqueous Solution Using Trimetaphosphate: Formation of Nucleoside Triphosphates," *J. Carbohydrates, Nucleosides, Nucleotides, 5*(2), 91–110 (1978); *Chem. Abstracts, 89*, p. 638, Abstract No. 180281m (1978); only Abstract supplied.* van der Woerd et al., Synthesis of $P^1$, $P^2$–Dinucleoside Pyrophosphates, *Tetrahedron Letters, 28*(24), 2763–2766 (1987).*

Quaedflieg et al., "Synthesis and Conformational Analysis of Phosphate–Methylated RNA Dinucleotides," *Journal of Organic Chemistry, 56*(20), 5846–5859 (1991).*

Iyer et al., "Methyl Phosphotriester Oligonucleotides: Facile Synthesis Using N–Pent–4–enoyl Nucleoside Phosphoramidites," *Journal of Organic Chemistry, 60*(25), 8132–8133 (1995).*

Lipkin et al., "The Base–catalyzed Alcohoholysis of Ribonucleic Acids. A Method for the Determination of End Groups," *J. of the American Chemical Society, 83*, 4771–4780 (Dec. 5, 1961).*

Perigaud et al., "Equal Inhibition of the Replication of Human Immunodeficiency Virus in Human T–Cell Culture by ddA bis(SATE)phosphotriester and 3'–azido–deooxythymidine," *Biochemical Pharmacology, 48*(1), 11–14 (Jul. 5, 1994).*

Malevskii et al., "Charge–Transfer Complexes of Nucleic Acid Nitrogen Bases and Their Analogs with Benzoquinone. Evidence of π–Donor Character," *Mol. Biol. (Moscow)15*(2), 447–453 (1981); *Chem. Abstracts, 94*(25), pp. 176–177, Abstr. No. 204014h (Jun. 22, 1981).*

Holy et al., "Oligonucleotide Compounds. XXIX. Reactions of Ribonucleoside 2'(3')–Phosphates With Dimethylformamide Acetals," *Collection of Czech. Chem. Comm., 34*(1), 253–271 (1989).*

Hecht et al., "Hydrolysis of Ribonucleoside 3'–Diphosphates by Rye Grass 3'–Nucleotidase," *Biochemistry, 14*(5), 974–981 (Mar. 11, 1975).*

Englund et al., "Enzymatic Synthesis of Deoxyribonucleic Acid," *Journal of Biological Chemistry, 244*(11), 3038–3044 (Jun. 10, 1969).*

Mitchel et al., "The Synthesis and Properties of Adenosine–2'–diphosphate and Adenosine–3'–diphosphate," *Canadian Journal of Biochemistry, 45*(1), 89–99 (1967); *Chem. Abstracts, 66*(9), p. 3307, Abstract No. 34846h (Feb. 27, 1967); only Abstract supplied.*

Josse et al., "Syntheses of Deoxynucleoside 3'–Triphosphates," *Biochemistry, 4*(12), 2825–2831 (Dec. 1965).*

R. A. Johnson et al. (IV), "Potent New Inhibitors of Adenylyl Cyclases Point to New Regulatory Pathways," Amer. Soc. Cell Biology 1994 Meeting., San Francisco, CA, Abstract No. 65, *Molecular Biology of the Cell, 5*(10, Supp.), p. 12a (Dec. 10–14, 1994).*

R. A. Johnson et al. (V), "Isozyme–Dependent Sensitivity of Adenylyl Cyclases to P–Site–Mediated Inhibition by Adenine Nucleotides and Nucleoside 3'–Polyphosphates," *Journal of Biological Chemistry, 272*(14), 8962–8966 (Apr. 4, 1997).*

Désaubry et al. (II), "Conjugation of Nucleoside Triphosphates to an Amino Linker," *Bioorganic &Medicinal Chem. Letters, 7*(2), 123–126 (Jan. 21, 1997).*

Désaubry et al. (III), "Inhibition of Adenylyl Cyclase by a Family of Newly Synthesized Adenine Nucleoside 3'–Polyphosphates," *Journal of Biological Chemistry, 271*(24), 14028–14034 (Jun. 14, 1996).*

Désaubry et al. (IV), "2', 5'–Dideoxyadenosine 3'–Polyphosphates Are Potent Inhibitors of Adenylyl Cyclases," *Journal of Biological Chemistry, 271*(5), 2380–2382 (Feb. 2, 1996).*

Désaubry et al. (V), "Synthesis of 2', 5'–Dideoxy–Adenosine–3'–Monophosphate Derivatives as Allosteric Inhibitors of Adenylyl Cyclase," *Nucleosides & Nucleotides, 14*(6), 1453–1460 (Aug. 1995).*

* cited by examiner

9-SUBSTITUTED ADENINE DERIVATIVES AS PRODRUG REGULATORS OF CELL AND TISSUE FUNCTION

This Application is a 371 of PCT/US01/21523 filed Jul. 6, 2001, which claims priority of U.S. Provisional Application Ser. No. 60/216,869 filed Jul. 7, 2000.

GOVERNMENT SUPPORT

Work leading to the present invention was supported in part by National Institutes of Health grant 2RO1DK38828 awarded by the National Institute of Diabetes & Digestive & Kidney Diseases. The United States government may have certain rights to this invention pursuant to the terms of that grant.

FIELD OF THE INVENTION

The present invention is directed to novel derivatives of adenine that inhibit adenylyl cyclase in cells but have little or no effect on isolated adenylyl cyclase. The present invention is also directed to methods for the use of these compounds to inhibit adenylyl cyclase dependent effects within cells.

BACKGROUND OF THE INVENTION

Adenosine-3':5'-cyclic monophosphate (3':5'-cAMP) is the second messenger mediating the transmembrane actions of numerous agents throughout the animal kingdom. It acts typically through the activation of 3':5'-cAMP-dependent protein kinases (PKA), which catalyze the phosphorylation of specific proteins [1,2] or through effects on 3':5'-cAMP-gated ion channels [3,4]. Consequently, relationships between 3':5'-cAMP and cell function are typically viewed as effects mediated by these two mechanisms. The 3':5'-cAMP signaling pathway can be regulated pharmacologically by many drugs that are of particular value in the treatment of various diseases and therefore there is continuing interest in identifying new agents acting on this pathway.

Cellular levels of 3':5'-cAMP are regulated by adenylyl cyclase, a family of membrane-bound enzymes that catalyze the formation of 3':5'-cAMP from 5'-ATP [5,6], and cyclic nucleotide phosphodiesterases, a family of enzymes that catalyze conversion of 3':5'-cAMP to 5'-AMP [7,8]. Agents that affect cellular 3':5'-cAMP levels, whether by affecting the activity of cyclic nucleotide phosphodiesterases or of adenylyl cyclases, also will typically affect changes in cell function.

Mammalian forms of adenylyl cyclase are a family of membrane-bound enzymes that catalyze the formation of 3':5'-cAMP from 5'-ATP. The family includes at least 10 isozymes and their expression is tissue dependent and developmentally variable. Activities of adenylyl cyclases are regulated by numerous neurotransmitters, autacoids, and hormones via cell surface receptors that act through heterotrimeric guanine nucleotide-dependent regulatory proteins (G-proteins; comprising $\alpha$, $\beta$, and $\gamma$ subunits). G-proteins may be either stimulatory ($G_s$) [9] or inhibitory ($G_i$) for adenylyl cyclase activity, and may be either specific or promiscuous in effecting activity of different isozymes [9–11]: $G_s\alpha$, for example, activates all isozymes, possibly save the isozyme from sperm. Adenylyl cyclase activity may also be altered by other agents of physiological and biochemical interest, including bacterial toxins that act on $G_S$ and $G_i$, agents or enzymes that act on hormone receptors, and agents that act directly on adenylyl cyclase, e.g. $Ca^{2+}$/calmodulin [12], forskolin [13,14], certain oxidants [15,16], protein kinases [17], and various adenine derivatives.

Numerous drugs have been developed as therapeutic agents that inhibit cyclic nucleotide phosphodiesterases [8]. There are also numerous therapeutically useful drugs that activate or inhibit adenylyl cyclases indirectly. One class of therapeutic agents having an indirect effect on adenylyl cyclases includes agents that are receptor blockers, such as agents that, for example, block receptors for catecholamines (dopamine, norepinephrine, and epinephrine), angiotensin II, adenosine and other purines. B-blockers that are commonly used to treat hypertension, for example, act to inhibit adenylyl cyclase indirectly by blocking the stimulatory effects of the sympathetic nervous system to activate adenylyl cyclase in the heart [5], in which the type V isozyme is expressed predominantly [6]. By comparison to drugs that inhibit cyclic nucleotide phosphodiesterases or that affect adenylyl cyclases indirectly, drugs that act directly on adenylyl cyclases are uncommon. The main class of such agents comprises analogs of forskolin [13,14].

Drugs that inhibit adenylyl cyclase directly would be particularly highly prized. The expectation is that such agents that act downstream of cell-surface receptors to inhibit adenylyl cyclase directly should have a cardiac-sparing effect and be useful in reducing cardiomyopathies and heart failure. We have developed a means to block the formation of 3':5'-cAMP in intact tissues by a unique class of specific and selective nucleotide prodrugs. These nucleotide prodrugs will find extensive use as pharmacologically and biochemically useful inhibitors of adenylyl cyclase. The prodrugs exhibit potencies in the nanomolar range and have shown their usefulness to regulate function in isolated cells and in intact tissues. Thus, the prodrugs of the invention are the most potent, directly acting inhibitors of adenylyl cyclases in tissues, and represent a new and unique class of drug with therapeutic potential.

Adenylyl cyclases are inhibited by a number of polyphosphorylated derivatives of adenine and adenosine (Table 1). Biochemical assays have been used to characterize inhibition of adenylyl cyclases by adenine derivatives with respect to ligand structures and inhibition kinetics [18–35]. The enzyme is inhibited competitively by substrate analogs that interact with a pre-transition configuration of the enzyme [31]. The most potent of these is $\beta$-L-2',3'-dd-5'-ATP (Table 1). In contrast, inhibition by adenine nucleoside 3'-phosphates bind to a post-transition configuration and inhibition is uncompetitive or non-competitive, depending on the mode of activation [25,26,33]. Potent inhibitors that bind selectively to pre- and post-transition states are extremely uncommon and because of this these compounds may form the basis of new inhibitors with unique biochemical and pharmacological properties.

TABLE 1

| | $IC_{50}$s for rat brain adenylyl cyclase | | |
|---|---|---|---|
| | NUCLEOSIDE ($IC_{50}$, μM) | | |
| 3'-Phosphate | Ado | 2'dAdo | 2',5'ddAdo |
| none | 82 | 15 | 2.7 |
| 3'~P | 8.9 | 1.2 | 0.46 |
| 3'~PP | 3.9 | 0.14 | 0.10 |
| 3'~PPP | 2.0 | 0.09 | 0.040 |
| 3'~PPPP | — | 0.0105 | 0.0074 |
| 3'~PS | — | 3.1 | 0.60 |

TABLE 1-continued

| IC$_{50}$s for rat brain adenylyl cyclase | |
|---|---|
| Substrate analogs: | IC$_{50}$ (µM) |
| β-L-5'-AMP | 200 |
| β-L-2',3'-dd-5'-AMP | 62 |
| β-L-5'-ATP | 3.2 |
| β-L-2',3'-dd-5'-ATP | 0.024 |
| PMEA-mimics: | IC$_{50}$ (µM) |
| PMEA | 65 |
| PMEApp | 0.17 |
| PMEAp(NH)p | 0.18 |

From Johnson and coll. [27–32]

The acyclic phosphonate derivatives of adenine, typified by PMEApp [32], are somewhat less potent than β-L-2',3'-dd-5'-ATP or 2',5'-dd-3'-ATP (Table 1), but the kinetic behavior of these agents conformed to mixed inhibition, i.e., kinetic behavior sharing aspects with that seen with the competitive and noncompetitive inhibitors. These distinctions form the basis for the rational design of compounds that can effect inhibition of adenylyl cyclases in intact tissues.

Crystal structures of the adenylyl cyclase catalytic cleft were solved in both pre- and post-transition states by use of β-L-2',3'-dd-5'-ATP and 2',5'dd-3'-ATP [36,37]. Note that there are only small differences in the topology of the catalytic cleft into which the respective ligands bind. It is presumed that PMEApp and its mimics bind in this same locus.

There are a number of cell-permeable derivatives of adenine that have been used to lower cellular 3':5'-cAMP levels and to alter function in isolated cells and intact tissues. These include 2',5'-dideoxyadenosine (2',5'-dd-Ado), 9-(tetrahydrofuryl)-adenine (9-THF-Ade;), 9-(arabinofurnosyl)-adenine (9-Ana-Ade), or 9-(cyclopentyl)-adenine (9-CP-Ate). These compounds am typically effective at concentrations from 10 to 100 µM. They have been used with epididymal fat cells [38], isolated hepatocytes [39], pre-adipocytes [40], thyroid follicles [41], dorsal root ganglion neurons [42], bone organ cultures [43], cortical collecting tubules [44], phagocytes [45], and platelets [20], to name but a few. End-points included cell differentiation [40], water conductance [44], action potential after-hyperpolarization [42], bone resorption [43], glycerol production [38], altered enzyme activity [39], DNA synthesis and cell growth [41], and FCγ-receptor-mediated phagocytosis [45]. Effects of these agents on cell function were uniformly consistent with inhibition of adenylyl cyclase by these ligands. The expectation is that the compounds of the invention will also affect cell function in these systems, but be substantially more potent in doing so.

SUMMARY OF THE INVENTION

The invention relates to 9-substituted adenine derivatives prodrugs that inhibit adenylyl cyclase in cells but have little or no effect on isolated adenylyl cyclase. The compounds preferably have a structure of formula (I) below:

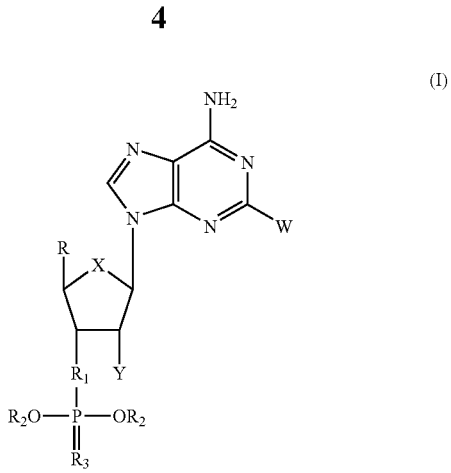

(I)

wherein W is selected from the group consisting of H, halogen, azido and amino group;

X is selected from the group consisting of O, S, N(H) and C;

Y is selected from the group consisting of H, hydroxy, $C_{1-4}$ alkyl, $C_{1-4}$ alkoxy and halogen;

R is selected from the group consisting of H, hydroxymethyl, $C_{1-4}$ alkyl, $C_{1-4}$ alkoxy and halogen;

$R_1$ is selected from the group consisting of O, NH and $CH_2$;

$R_2$ represents a radical selected from the group consisting of —(CH$_2$)$_n$—S—C(O)—R$_4$ and —(CH$_2$)$_n$—S—S—R$_4$, where n=1–4 and R$_4$ is a $C_{1-4}$ alkyl or aryl group and R$_4$ is optionally substituted with a halogen, amino, N-alkylamino, N, N di-alkylamino or $C_{1-4}$ alkoxy group, and wherein each of the R$_2$ radicals may be the same or different; $R_3$ is O or S; and when X is C the cyclopentyl ring so formed may be saturated or unsaturated.

The following are independent preferences.

The preferred group that W represents is H.

A preferred alkoxy group that Y or R represents is methoxy. A preferred alkyl group that Y or R represents is methyl.

Also preferred is where $R_4$ is selected from the group consisting of unsubstituted $C_{1-4}$ alkyl and unsubstituted aryl groups. Still more preferred is where $R_4$ is selected from the group consisting of methyl, tert-butyl and phenyl groups.

The preferred value for n is 2.

Also preferred is where, simultaneously, Y is selected from the group consisting of H, hydroxy, methyl, methoxy and halogen; and R is selected from the group consisting of H, methyl, hydroxymethyl, methoxy and halogen.

Still more preferred is where, simultaneously, Y is selected from the group consisting of H, hydroxy, methyl, methoxy and halogen; R is selected from the group consisting of H, methyl, hydroxymethyl, methoxy and halogen; R4 is selected from the group consisting of methyl, tert-butyl and phenyl; and n=2.

Still more preferred is where, simultaneously, W represents a hydrogen atom; Y is selected from the group consisting of H, hydroxy, methyl, methoxy and halogen; R is selected from the group consisting of H, methyl, hydroxymethyl, methoxy and halogen; R4 is selected from the group consisting of methyl, tert-butyl and phenyl; and n=2.

In certain embodiments, a compound of the invention is selected from the group consisting of

- 2',5'-dideoxy-β-(L)-adenosine 3'-monophosphate-bis(Me-SATE);
- 2',5'-dideoxy-β-(D)-adenosine 3'-monophosphate-bis(MC-SATE);
- 2'-deoxy-β-(L)-adenosine 3'-monophosphate-bis(Me-SATE);
- 2'-deoxy-β-(D)-adenosine 3'-monophosphate-bis(Me-SATE);
- 2',5'-dideoxy-β-(L)-adenosine 3'-monophosphate-bis(t-Bu-SATE);
- 2',5'-dideoxy-β-(D)-adenosine 3'-monophosphate-bis(t-Bu-SATE);
- 2'-deoxy-β-(L)-adenosine 3'-monophosphate-bis(t-Bu-SATE);
- 2'-deoxy-β-(D)-adenosine 3'-monophosphate-bis(t-Bu-SATE);
- 2',5'-dideoxy-β-(L)-adenosine 3'-monophosphate-bis(Ph-SATE);
- 2',5'-dideoxy-β-(D)-adenosine 3'-monophosphate-bis(Ph-SATE);
- 2'-deoxy-β-(L)-adenosine 3'-monophosphate-bis(Ph-SATE);
- 2'-deoxy-β-(D)-adenosine 3'-monophosphate-bis(Ph-SATE);
- 2',5'-dideoxy-β-(L)-adenosine 3'-methylene phosphate-bis(Me-SATE);
- 2',5'-dideoxy-β-(D)-adenosine 3'-methylene phosphate-bis(Me-SATE);
- 2'-deoxy-β-(L)-adenosine 3'-methylene phosphate-bis(Me-SATE);
- 2'-deoxy-β-(D)-adenosine 3'-methylene phosphate-bis(Me-SATE);
- 2',5'-dideoxy-β-(L)-adenosine 3'-methylene phosphate-bis(t-Bu-SATE);
- 2',5'-dideoxy-β-(D)-adenosine 3'-methylene phosphate-bis(t-Bu-SATE);
- 2'-deoxy-β-(L)-adenosine 3'-methylene phosphate-bis(t-Bu-SATE);
- 2'-deoxy-β-(D)-adenosine 3'-methylene phosphate-bis(t-Bu-SATE);
- 2',5'-dideoxy-β-(L)-adenosine 3'-methylene phosphate-bis(Ph-SATE);
- 2',5'-dideoxy-β-(D)-adenosine 3'-methylene phosphate-bis(Ph-SATE);
- 2'-deoxy-β-(L)-adenosine 3'-methylene phosphate-bis(Ph-SATE);
- 2'-deoxy-β-(D)-adenosine 3'-methylene phosphate-bis(Ph-SATE);
- 2',5'-dideoxy-β-(L)-adenosine 3'-iminophosphate-bis(Me-SATE);
- 2',5'-dideoxy-β-(D)-adenosine 3'-iminophosphate-bis(Me-SATE);
- 2'-deoxy-β-(L)-adenosine 3'-iminophosphate-bis(,Me-SATE);
- 2'-deoxy-β-(D)-adenosine 3'-iminophosphate=bis(Me-SATE);
- 2',5'-dideoxy-β-(L)-adenosine 3'-iminophosphate-bis(t-Bu-SATE);
- 2',5'-dideoxy-β-(D)-adenosine 3'-iminophosphate-bis(t-Bu-SATE);
- 2'-deoxy-β-(L)-adenosine 3'-iminophosphate-bis(t-Bu-SATE);
- 2'-deoxy-β-(D)-adenosine 3'-iminophosphate-bis(t-Bu-SATE);
- 2',5'-dideoxy-β-(L)-adenosine 3'-iminophosphate-bis(Ph-SATE);
- 2',5'-dideoxy-β-(D)-adenosine 3'-iminophosphate-bis(Ph-SATE);
- 2'-deoxy-β-(L)-adenosine 3'-iminophosphate-bis(Ph-SATE); and
- 2'-deoxy-β-(D)-adenosine 3'-iminophosphate-bis(Ph-SATE).

In other embodiments, a compound of the invention is selected from the group consisting of:

- 9-(tetrahydrofuryl)-(1'R,3'S)-adenine-3'-phosphate-bis(Me-SATE);
- 9-(tetrahydrofuryl)-(1'R,3'R)-adenine-3'-phosphate-bis(Me-SATE);
- 9-(tetrahydrofuryl)-(1'R,3'S)-adenine-3'-phosphate-bis(t-Bu-SATE);
- 9-(tetrahydrofuryl)-(1'R,3'R)-adenine-3'-phosphate-bis(t-Bu-SATE);
- 9-(tetrahydrofuryl)-(1'R,3'S)-adenine-3'-phosphate-bis(Ph-SATE);
- 9-(tetrahydrofuryl)-(1R,3'R)-adenine-3'-phosphate-bis(Ph-SATE);
- 9-(tetrahydrofuryl)-(1R,3'S)-adenine-3'-($CH_2$)phosphate-bis(Me-SATE);
- 9-(tetrahydrofuryl)-(1'R,3'R)-adenine-3'-($CH_2$)-phosphate-bis(Me-SATE);
- 9-(tetrahydrofuryl)-(1'R,3'S)-adenine-3'-($CH_2$)-phosphate-bis(t-Bu-SATE);
- 9-(tetrahydrofuryl)-(1'R,3'R)-adenine-3'-($CH_2$)phosphate-bis(t-Bu-SATE);
- 9-(tetrahydrofuryl)-(1'R,3'S)-adenine-3'-($CH_2$)-phosphate-bis(t-Ph-SATE);
- 9-(tetrahydrofuryl)-(1'R,3'R)-adenine-3'-($CH_2$)-phosphate-bis(t-Ph-SATE);
- 9-(tetrahydrofuryl)-(1'R,3'S)-adenine-3'-(NH)-phosphate-bis(Me-SATE);
- 9-(tetrahydrofuryl)-(1'R,3'R)-adenine-3'-(NH)-phosphate-bis(Me-SATE);
- 9-(tetrahydrofuryl)-(1'R,3'S)-adenine-3'-(NH)-phosphate-bis(t-Bu-SATE);
- 9-(tetrahydrofuryl)-(1'R,3'R)-adenine-3'-(NH)-phosphate-bis(t-Bu-SATE);
- 9-(tetrahydrofuryl)-(1'R,3'S)-adenine-3'-(NH)-phosphate-bis(Ph-SATE); and
- 9-(tetrahydrofuryl)-(1'R,3'R)-adenine-3'-(NH)-phosphate-bis(Ph-SATE).

In still other embodiments of the invention, a compound is selected from the group consisting of:

- 9-(cyclopentyl)-(1'R,3'S)-adenine-3'-phosphate-bis(Me-SATE);
- 9-(cyclopentyl)-(1'R,3'R)-adenine-3'-phosphate-bis(Me-SATE);
- 9-(cyclopentyl)-(1'R,3'S)-adenine-3'-phosphate-bis(t-Bu-SATE);
- 9-(cyclopentyl)-(1'R,3'R)-adenine-2'-phosphate-bis(t-Bu-SATE);
- 9-(cyclopentyl)-(1'R,3'S)-adenine-3'-phosphate-bis(Ph-SATE);

9-(cyclopentyl)-(1'R,3'R)-adenine-3'-phosphate-bis(Ph-SATE);

9-(cyclopentyl)-(1'R,3'S)-adenine-3'-(CH$_2$)phosphate-bis(Me-SATE);

9-(cyclopentyl)-(1'R,3'R)-adenine-3'-(CH$_2$)-phosphate-bis(Me-SATE);

9-(cyclopentyl)-(1'R,3'S)-adenine-3'-(CH$_2$)-phosphate-bis(t-Bu-SATE);

9-(cyclopentyl)-(1'R,3'R)-adenine-3'-(CH$_2$)-phosphate-bis(t-Bu-SATE);

9-(cyclopentyl)-(1'R,3'S)-adenine-3'-(CH$_2$)-phosphate-bis(t-Ph-SATE);

9-(cyclopentyl)-(1'R,3'R)-adenine-3'-(CH$_2$)-phosphate-bis(t-Ph-SATE);

9-(cyclopentyl)-(1'R,3'S)-adenine-3'-(NH)-phosphate-bis(Me-SATE);

9-(cyclopentyl)-(1'R,3'R)-adenine-3'-(NH)phosphate-bis(Me-SATE);

9-(cyclopentyl)-(1'R,3'S)-adenine-3'-(NH)-phosphate-bis(t-Bu-SATE);

9-(cyclopentyl)-(1'R,3'R)-adenine-3'-(NH)-phosphate-bis(t-Bu-SATE);

9-(cyclopentyl)-(1'R,3'S)-adenine-3'-(NH)-phosphate-bis(Ph-SATE); and 9-(cyclopentyl)-(1'R,3'R)-adenine-3'-(NH)-phosphate-bis(Ph-SATE).

In another aspect, the invention provides methods of reducing or inhibiting adenylyl cyclase activity in intact cells and tissues comprising the steps of contacting cells or tissues with a compound of the invention for a period of time and under such conditions such that the adenylyl cyclase activity is reduced or inhibited.

In yet another aspect, the invention provides compounds, compositions and methods for regulating cardiac function or performance.

The invention also provides methods of altering the growth; development or differentiation of cells and tissues by administering a compound of the invention.

Naturally, as used herein, administration of a compound of the invention is meant to encompass the instances where a compound of the invention is administered alone, in combination with one or more other compounds of the invention or in conjunction with other compounds.

DETAILED DESCRIPTION OF THE INVENTION

All U.S. patents and other publications cited herein are hereby incorporated by reference in there entirety. In the case of inconsistencies in definitions, the present description will control.

It is further understood that all compounds described, listed and represented herein are meant to include all hydrates, solvates, polymorphs and pharmaceutically acceptable salts thereof.

Some compounds described herein contain one or more asymmetric centers and may thus give rise to diastereomers and optical isomers. The present invention is meant to comprehend such possible diastereomers as well as their racemic and resolved, enanteomerically pure forms and pharmaceutically acceptable salts thereof.

Some of the compounds described herein contain olefinic double bonds and, unless otherwise specified, are meant to include both E and Z geometric isomers.

Because tissues and cells are typically impermeable to charged molecules, phosphorylated adenine derivatives are generally taken up poorly by cells and so typically they exhibit little effect on cells. To circumvent this problem, we applied techniques currently being used in the development of nucleoside-based antiviral therapeutics to create cell permeable precursors of adenylyl cyclase inhibitors. The idea is that these compounds, which are inactive on the isolated enzyme, will enter cells and be metabolically converted into more potent compounds that then effect changes in cell function. Nucleotide prodrugs have protected phosphate groups to afford the molecule cell permeability. Once a protected nucleoside monophosphate is inside the cell the protecting group is cleaved and the nucleotide is then converted to a more potent form by intracellular enzymes (Gosselin et al., U.S. Pat. No. 5,849,905).

In preferred embodiments, protection of phosphorylated compounds can be achieved through thin-ethyl linkages. One protection group is, for example, the S-acyl-thioethyl group, where the aryl group may be any of several moieties, e.g. tert-butylacyl, methylacyl or phenylacyl, etc. This agent undergoes cleavage by carboxyesterases at the S-acyl bond, thereby allowing the intramolecular attack of the sulfur on the phosphate group to yield the leaving of the thin-ethyl group. The phosphate group is then free to participate in other reactions within the cell, e.g. phosphorylation.

A parallel set of reactions occurs if an alklydithioethyl group is used as protective ligand. In this instance cleavage occurs between the two sulfur atoms by the action of cellular reductases. The resultant free thiol may then undergo intramolecular attack of phosphate group with subsequent leaving of the thioethyl group and freeing of the phosphate group [50,55].

U.S. Pat. Nos. 5,770,725 and 5,849,905 to Gosselin et al. disclose biologically active phosphotriester-type nucleosides and methods for preparing the same. U.S. Pat. No. 5,795,756 to Johnson et al. discloses a method and compounds for the inhibition of adenylyl cyclase.

Though there are many prodrug derivatives of adenine and adenosine with potential as intracellular inhibitors of adenylyl cyclases, we found that only one group of compounds exhibited the appropriate behavior of acting as very weak inhibitors of adenylyl cyclase when tested on isolated enzyme but having potent effects when tested on intact cells. The prodrugs of the invention are among the most potent agents for inhibiting adenylyl cyclase dependent events in cells.

The prodrugs of the invention comprise the base adenine. Substitutions on the adenine base will typically compromise the ability of a prodrug or a dc-protected prodrug-derivative to act as an inhibitor of adenylyl cylcase. However, adenine derivatives substituted at the 2-position of the adenine base with an amino, cyano or halogen atom may retain adenylyl cyclase inhibitory activity.

Families of ligands were made based on derivatives of:

i) 9-(phosphonomethoxyethyl)-adenine (PMEA); ii) β-L-adenosine; and iii) 2',5'-dideoxy adenosine (2',5'-dd-Ado).

Prodrug structures. We have adapted the following protecting substituents for derivatization of adenine:

i) tert-butyl-(S-acyl-2-thioethyl); (t-Bu-SATE-)

ii) methyl-(S-acyl-2-thioethyl); (Me-SATE-)

iii) phenyl-(S-aryl-2-thioethyl); (Ph-SATE-)

iv) cyclosalicyl; (H-Sal-)

v) 3-methyl-cyclosalicyl; (Me-Sal-)

These will yield the following compounds:
1) 2',5'-dd-3'-AMP-bis(Me-SATE)
2) 2',5'-dd-3'-AMP-bis(t-Bu-SATE)
3) 2',5'-dd-3'-AMP-bis(Ph-SATE-)
4) β-L-2',5'-dd-3'-AMP-bis(Me-SATE)
5) β-L-2',5'-dd-3'-AMP-bis(t-Bu-SATE)
6) β-L-2',5'-dd-3'-AMP-bis(Ph-SATE)
7) β-L-2',3'-dd-5'-AMP-bis(Me-SATE)
8) β-L-2',3'-dd-5'-AMP-bis(tBuSATE)
9) β-L-2',3'-dd-5'-AMP-bis(Ph-SATE)
10) 2',5'-dd-3'-AMP-(H-Sal)
11) 2',5'-dd-3'-AMP-(Me-Sal)
12) bis(Me-SATE)-9-(2-phosphonomethoxyethyl)-adenine; (Me-SATE-PMEA) [46]
13) bis(t-Bu-SATE)-9-(2-phosphonomethoxyethyl)-adenine; (t-Bu-SATE-PMEA)[46]
14) bis(Ph-SATE)-9-(2-phosphonomethoxyethyl)-adenine; (Ph-SATE-PMEA) [46]
15) bis(Me-SATE)-9-(2-phosphonomethoxypropyl)-adenine; (Me-SATE-PMPA)
16) bis(t-Bu-SATE)-9-(2-phosphonomethoxypropyl)-adenine; (t-Bu-SATE-PMPA)
17) bis(Ph-SATE)-9-(2-phosphonomethoxypropyl)-adenine; (Ph-SATE-PMPA)

Of these 1), 2), 3), 5), 8), 10), 11), 12), 13), 14), and 16) have been synthesized.

The examples shown below illustrate the invention as described in this text, with no intention to limit it.

EXAMPLE 1

Prodrug Syntheses a. 2.5'-dideoxyadenosine-3'-O-bis(S-acyl-2-thioethyl)-phosphates (compounds 1–3). To a stirred solution of 2',5'-dideoxyadenosine (100 mg, 0.42 mmol) in a mixture of tetrahydrofurane and dimethylformamide (1.5 ml, 1:05, v/v) was added 1H-tetrazole (88 mg, 1.26 mmol, 3.0 eq) followed by the dropwise addition at room temperature of a solution of the bis(S2-hydroxyethylthioacyl) N,N-diisopropylphosphoramidite (0.51 mmol, 1.25 eq of -acetyl-: 188 mg (for compound 1); -pivaloyl-: 230 mg (for compound 2); or -benzoyl-: 252 mg (for compound 3)) in 0.5 ml tetrahydrofuran. The reaction mixture was stirred for 45 min and then cooled to −40° C. and tert-butylhydroperoxide (0.44 ml, 1.26 mmol, 3.0 eq, 90% in tert-butanol) was added. The reaction mixture was stirred for 30 min at room temperature, diluted with 30 ml dichloromethane and washed with 10 ml of a 10% aqueous sodium sulfite and then 10 ml water. The organic phase was dried with sodium sulfate and evaporated to dryness under reduced pressure. The residue was purified by column chromatography with silica gel with a stepwise gradient of 0 to 4% methanol in dichloromethane. The products were isolated as colorless foams.

(i) 2',5'-dideoxyadenosine-3'-O-bis(S-acetyl-2-thioethyl) phosphate (Compound 1): Yield, 100 mg (0.19 mmol, 46%); TLC: $R_f$=0.37 (methylenechloride/methanol=93:7, v/v), $R_f$=0.16 (ethyl acetate/methanol=95:5, v/v). HPLC: Rt=34.2 min, $^1$H NMR (DMSO-$d_6$): δ=8.35 and 8.16 (2s, 1H each, H-2 and H-8), 7.30 (br s, 2H, NH$_2$), 6.32 (t, J=6.9 Hz, 1H, H-1'); 4.96–4.94 (m, 1H, H-3'), 4.23–4.19 (m, 1H H4'), 4.15–4.07 (m, 4H, CH$_2$O), 3.26–3.15 (m, 1H, H-2' partially obscured by t, J=6.3 Hz, 4H, CH$_2$S), 2.64–2.57 (m, 1H-2"), 2.36 and 2.35 (2s, 3H each, 2 CH$_3$ acetyl), 1.34 (d, J=6.4 Hz, 3H, CH$_2$). $^{31}$P NMR (DMSO-$d_6$): δ=−1.47. Elemental analysis: $C_{18}H_{26}N_5O_7PS_2$ (519.54); calcd. C41.61, H 5.04, N 13.48.

ii) 2,5'-dideoxyadenosine-3'-O-bis(S pivaloyl-2-thioethyl) phosphate (Compound 2): Yield, 190 mg (0.31 mmol, 75%); TLC: $R_f$=0.45 (methylenechloride/methanol=93:7, v/v), $R_f$=0.27 (ethyl acetate/methanol=95:5, v/v), HPLC: Rt=42.8 min. $^1$H NMR (DMSO-$d_6$): δ=8.56 and 8.35 (2s, 1H each, H-2 and H-8), 6.37 (t, J=6.7 Hz, 1H, H-1'), 4.95 (m, 1H-3'), 4.25–4.22(m, 1H, H-4'), 4.14–4.06 (m, 4H, CH$_2$O), 3.59 (br s, 2H, NH$_2$), 3.18–3.13 (m, 1H, H-2' partially obscured by t, J=6.2 Hz, 4H, CH$_2$S), 2,68–2.64 (m, 1H, H-2"), 1.35 (d, J=6.4 Hz, 3H, CH$_2$), 1.18 and 1.16 (2s, 9H each, 2 C(CH$_3$)$_3$). $^{31}$P NMR (DMSO-$d_6$): δ=−1.47. Elemental analysis: $C_{24}H_{38}N_5O_7PS_2$ (603.70), calcd. C 47.75, H 6.34, N 11.60.

(iii) 2',5'-dideoxyadenosine-3'-O-bis(S-benzoyl-2-thioethyl) phosphate (Compound 3): Yield, 170 mg (0.26 mmol, 63%); TLC: $R_f$=0.33 (methylenechloride/methanol=93:7, v/v), $R_f$=0.19 (ethyl acetatelmethanol=95:5, v/v), HPLC: Rt=41.6 min. $^1$H NMR (DMSO-$d_6$): δ=8.31 and 8.14 (2s, 1 H each, H-2 and H-8), 7.92–7,87, 7,69–7.64, 7.56–7.48 (m, 10H, 2 $C_6H_5$), 7.30 (br s, 2H, NH$_2$) 6.30 (t, J=6.9 Hz, 1H H-1'), 4.97 (m, 1H, H-3'), 4.29–4.19 (m, 5H, H-4' and CH$_2$O), 3.41(t, J=6.1 Hz, 4H, CH$_2$S), 3.26–3.13 (m, 1H, H-2'), 2.62–2.54 (m, 1H, H-2"), 1.29 (d, J=6.8 Hz, 3H, CH$_3$). $^{31}$P NMR (DMSO-$d_6$); δ=−1.44. Elemental analysis: $C_{28}H_{30}N_5O_7PS_2$ (643.68); calcd. C 52.25, H 4.70, N 10.88.

b. 2',5'-dideoxyadenosine-3'-O-cyclosaligenyl Phosphates (compounds 10 and 11). To a stirred solution of 2',5'-dideoxyadenosine (141 mg, 0.60 mmol) in 10 ml dimethylformamide was added diisopropylethylamine (116 mg, 0.90 mmol, 1.5 eq) followed by the dropwise addition at −40° C. of a solution of the cyclic chlorophosphane (0.90 mmol, 1.5 eq/unsubstituted: 170 mg (for compound 10); -3-methyl-182 mg (for compound 11)) in 1 ml tetrahydrofuran. The reaction mixture was stirred for 30 min and tert-butylhydroperoxide (0.2 ml, mmol, eq, 90% in tert-butanol) was added. The reaction mixture was stirred for 30 min at room temperature and evaporated to dryness under reduced pressure. The residue was purified by column chromatography with silica gel using a stepwise gradient of 0 to 4% methanol in dichloromethane. The products were isolated as colorless foams.

(i) 2',5'-dideoxyadenosine-3.0-cyclosaligenyl phosphate (Compound 10). Yield, 190 mg (0.47 mmol, 79%); TLC: $R_f$=0.29 (methylenechloride/methanol=93:7, v/v), $R_f$=0.16 (ethyl acetate/methanol=95:5, v/v). HPLC: Rt=33.2 min. $^1$H NMR (DMSO-$d_6$): δ=8.69, 8.34, 8.32 and 8.12(s, 2H, H-2 and H-8, two diastereomers), 7.44–7.05 (m, 5H, 3H $C_6H_4$ and NH$_2$), 6.89–6.73 (m, 1H,1H $C_6H_4$), 6.33–6.27 (m, 1H, H-1'), 5.58–5.30 (m, 2H, CH$_2$), 5.15 (m, 1H, H-3'), 4.26–4.15 (m, 1H, H-4'), 3.23–3.17 (m, 1 H, H-2'), 2.68–2.61 (m, 1H, H-2"), 1.34–1.24 (m, 3H, CH$_3$). $^{31}$P NMR (DMSO-$d_6$); δ=−9.56, −9.60. Elemental analysis: $C_{17}H_{18}N_5O_5P$ (403.34); calcd. C 50.63, H 4.50, N 17.36.

(ii) 2',5'-dideoxyadenosine-3'-O-cyclo-3-methyl-saligenyl phosphate (Compound 11). Yield, 200 mg (0.48 mmol, 80%); TLC: $R_f$=0.31 (methylenechloride/methanol=93:7, v/v), $R_f$=0.17 (ethyl acetate/methanol=95:5, v/v); HPLC: Rt=34.1 min. $^1$H NMR (DMSO-$d_6$): δ=8.65, 8.33, 8.32 and 8.12 (s, 2H, H-2 and H-8, two diastereomers), 7.30–7.03 and 6.72 (m, 5H, 3H $C_6H_3$ and NH$_2$), 6.30–6.27 (m, 1H, H-1'),5.54–5.48 (m, 2H, CH$_2$), 5.18–5.15 (m, 1H, H-3'), 4.22–4.11 (m, 1H, H-4'), 3.29–3.21 (m, 1H, H-2'), 2.67–2.60 (m, 1H, H-2"), 2.27–2.15 (m, 3H, CH, saligenyl), 1.37–1.25 (m, 3H, CH$_3$). $^{31}$P NMR (DMSO-d$_6$); δ=–8.98, –9.02. Elemental analysis: C$_{18}$H$_{20}$N$_5$O$_5$P (417.36); calcd. C 51.80, H 4.83, N 16.78.

c. β-L-2',3'-dideoxyadenosine-5'-O-bis(S-aryl-2-thioethyl)-phosphate (compounds 7–9). To a stirred solution of β-L-2',3'-dideoxyadenosine (44 mg, 0.187 mmol) in a mixture of tetrahydrofuran and dimethylformamide (1.5 ml, 2:1, v/v) was added 1 H-tetrazole (39 mg, 0.56 mmol, 3.0 eq) followed by the dropwise addition at room temperature of a solution of the appropriate bis(S-2-hydroxyethylthioacyl) N,N-diisopropylphosphoramidite. For β-L-2',3'-dideoxyadenosine-5'-O-bis(S-pivaloyl-2-thioethyl)-phosphate (or β-L-2',3'dd-5'-AMP-bis(tBu-SATE), compound 8) this was bis(S-2-hydroxyethylthiopivaloyl) N,N-diisopropylphosphoramidite (127 mg, 0.28 mmol, 1.5 eq) in 0.5 ml tetrahydrofuran. The reaction mixture was stirred for 45 min and then cooled to –40° C. and tert-butylhydroperoxide (45 ml, 0.45 mmol, 2.4 eq, 90% in tert-butanol) was added. The reaction mixture was stirred for 30 min at room temperature, diluted with 30 ml dichloromethane and washed with 10 ml of a 10% aqueous sodium sulfite and then 10 ml water. The organic phase was dried with sodium sulfate and evaporated to dryness under reduced pressure. The residue was purified by column chromatography with silica gel using a stepwise gradient of 0 to 4% methanol in dichloromethane, The product (compound 8) was isolated as a colorless foam. Syntheses of β-L-2',3'-dideoxyadenosine-5'-O-bis(S-acetyl-2-thioethyl)-phosphate (or β-L-2',3'-dd-5'-AMP-bis(Me-SATE), compound 7) and β-L-2',3'dideoxyadenosine-5'-O-bis(S-benzoyl-2-thioethyl)-phosphate (or β-L-2',3'-dd-5'-AMP-bis (tBu-SATE), compound 9) follow from the respective bis (S-2-hydroxyethylthioacyl) N,N-diisopropylphosphoramidites in a similar fashion.

β-L-2', 3'-dideoxyadenosine-3'-O-bis(S-pivaloyl-2-thioethyl) phosphate (Compound 8). Yield, 60 mg (0.099 mmol, 53%); TLC: R$_f$=0.32 (methylene-chloride/methanol=93:7, v/v), R$_f$=0.14 (ethyl acetatelmethanol=95:5, v/v), HPLC: Rt=41.1 min. $^1$H NMR (DMSO-d$_6$): δ=8.40 and 8.28 (2s, 1H each, H-2 and H-8), 7.96 (br s, 2H, NH$_2$), 6.28 (t, J=5.2 HZ, 1H, H-1'), 4.31 (m, 1H, H-4'), 4.19–4.08 (m, 2H, 2H-3'), 4.01–3.93 (m, 4H, CH$_2$O), 3.06 (t, J=6.1 Hz, 4H, CH$_2$S), 2.51 (m, 2H, 2 H-5'), 2.18–2.11 (m, 2H, 2 H-2'), 1.16 and 1.15 (2s, 9H each, 2 C(CH$_3$)3). $^{31}$P NMR (DMSO-d$_6$): δ=–0.59. Elemental analysis: C$_{24}$H$_{38}$N$_5$O$_7$PS$_2$ (603.70); calcd. C 47.75, H 6.34, N 11.60.

d. (R)-Bis(S-pivaloyl-2-thioethyl) 9-(2-phosphonylmethoxypropyl)adenine (Compounds 15–17). For the synthesis of the -pivaloyl-derivative (compound 16) a mixture of monotriethylammonium N$^6$-(4-monomethoxytrityl)-9-(2-phosphonylmethoxypropyl) adenine (86 mg, 0.13 mmol) and S-pivaloyl-2-thioethanol (105 mg, 0.65 mol, 5.0 eq) was coevaporated three times with 5 ml pyridine each and dissolved in 1.5 ml of dry pyridine. After addition of 1-(mesitylenesulfonyl)-3-nitro-1H-1,2,4-triazole (193 mg, 0.65 mmol, 5.0 eq) the reaction mixture was stirred for 3 d at ambient temperature. The reaction was stopped by addition of 20 ml saturated aqueous sodium bicarbonate and the resulting mixture was extracted with 30 ml methylenechloride. The organic phase was dried by filtration through MgSO$_4$ and evaporated to dryness. The residue was purified by flash chromatography (20 g silica gel) with a stepwise gradient of 0 to 4% methanol in methylenechloride. Appropriate fractions were combined and evaporated to dryness, The residue was dissolved in 5 ml of a mixture of acetic acid/water/methanol=8:1:1 (v:v:v). The reaction mixture was stirred for 24 h at ambient temperature. The solvent was evaporated in vacuo and the residue was coevaporated twice with 5 ml toluene, twice with 5 ml methanol and then with 5 ml methylenechloride. The residue was purified by flash chromatography (15 g silica gel) with a stepwise gradient of 0 to 20% methanol in methylenechloride yielding 48 mg (R)-bis(S-pivaloyl 2-thioethyl) 9-(2-phosphonylmethoxypropyl)-adenine (compound 16); 0.083 mmol, 64%) as colorless oil. Synthesis of (R)-bis(S-acetyl-2-thioethyl)-9(2-phosphonoylmethoxy-propyl)-adenine (compound 15) and (R)-bis(S-benzoyl-2-thioethyl)-9-(2-phosphonyl-methoxypropyl)-adenine (compound 17) follow from the respective S-aryl-2-thioethanol in a similar fashion.

(R)-Bis(S-pivaloyl-2-thioethyl) 9-(2-phosphonylmethoxypropyl)-adenine. (Compound 16) TLC: R$_f$=0.28 (methylenechloridelmethanol=93:7, v/v), R$_f$=0.08 (ethyl acetatelmethanol=95:5, v/v), HPLC: Rt=40.6 min. $^1$H NMR (DMSO-d$_6$): δ=8.14 and 8.06 (2s, 1H each, H-2 and H-8), 7.23 (br s, 2H, NH$_2$), 4.25–4.18 (m, 2H, NCH$_2$), 3.99–3.85 (m, 7H, CH$_3$CH, PCH$_2$, 2 CH$_2$O), 3.07–3.00 (m, 4H, CH$_2$S), 1.17 (s, 18H, 2 C(CH$_3$)$_3$), 1.09 (d, J=6.2 Hz, 3H, CH$_3$). $^{31}$P NMR (DMSO-d$_6$): δ=22.97; Elemental analysis: C$_{23}$H$_{38}$N$_5$O$_6$PS$_2$ (575.69); calcd. C 47.99, H 6.65, N 12.17.

e. General methods for synthesis of compounds 1–3 and 7–17. $^{31}$P (101 MHz) and $^1$H NMR (250 MHz): Bruker AC250; the residual solvent peaks were used as internal standard for the $^1$H NMR spectra, phosphoric acid was used as external standard for the $^{31}$P NMR spectra. All $^{31}$P NMR spectra were recorded in the proton-decoupled mode. Chemical shifts are given in δ (ppm) and coupling constants, J, are in Hz. Column chromatography was carried out on silica gel 60 (particle size 0.040–0.063 mm; EM Science, Merck, Darmstadt). Analytical thin-layer chromatography, used to monitor all reactions, was performed on silica get 60 PF$_{254}$, with fluorescence indicator (0.2 mm; Merck, Darmstadt) on aluminum plates, and visualization was accomplished by UV absorbance. Phosphorus containing compounds were detected by spraying with Hanes molybdate reagent. Sugar containing compounds were detected by spraying with anisaldehyde reagent each time followed by heating. High-performance liquid chromatography (HPLC) studies were carried out on a Waters system equipped with a model 600 controller, a model 717plus autosampler, a model 996 photodiode array detector and a Millenium data workstation. Separations were by reverse-phase chromatography (Ultrasphere, C18, 250×4.6 mm, 5 μm) with linear gradients of 0 to 100% acetonitrile in water over a 40 min period at a flow rate of 1 ml/min. S-acyl-2-thioethanols and bis(S-2-hydroxyethylthioacyl) N,N-diisopropylphosphoramidites were synthesized according to Lefebvre et al.[50]. The cyclic chlorophosphanes were synthesized according to Meier [51]. 2',5'-dideoxyadenosine was synthesized according to Désaubry et al. [52]. Monotriethylammonium N$^6$-(4-monomethoxytrityl)-9-(2-phosphonylmethoxypropyl)-adenine was synthesized according to Holy et al. [53,54]. Solvents: pyridine, tetrahydrofuran and dimethylformamide were analytical quality, absolute from Fluke. 1H-tetrazole and 1-(mesitylenesulfonyl)-3-nitro-1H-1,2,4-triazole were from Aldrich.

f. Syntheses of 9-(2',5'-dideory-β-L-erythropentoforanosyl)-adenine (β-L-2',5'-dideoxyadenosine) and its tert-Bu-SATE (compound 5). (i) 9-(2',5'-dideoxy-β-L-erythro-pentofuranosyl)adenine. By use of the procedure previously described in the D-series by Désaubry et al. [52], β-L-2'-deoxyadenosine (0.7 g, 2.8 mmol) was dissolved in pyridine (10 ml) and treated with diphenyldisulfide (0.76 g, 3.5 mmol) and tributylphosphine (0.87 ml, 3.5 mmol). After 24 h, methanol (10 ml) was added, the solution was concentrated to dryness and coevaporated with toluene, then with methanol. Crude material was purified by silica gel column chromatography using a stepwise gradient of 0 to 12% methanol in dichloromethane to give pure thio intermediate (0.70 g, 73%). The thio intermediate (0.7 g, 2.04 mmol) was dissolved in a mixture of methanol-isopropanol (1/1, v/v, 10 ml) and treated with Raney Nickel. (1 g). The suspension was refluxed for 10 days, then Nickel was removed and washed by three portions of boiling methanol. The combined filtrates were concentrated to dryness and the residue was purified by silica gel column chromatography with an isocratic gradient of 10% methanol in dichloromethane to give pure 9-(2,5-dideoxy-β-L-erythro-pentofuranosyl)-adenine 1 (282 mg, 59%).

β-L-2,5'-dideoxyadenosine. $R_f$(MeOH/CH$_2$Cl$_2$, 15/85)= 0.33; mp 173° C.; UV (EtOH 95) λmax 260 nm (ε, 14600), λmin 227nm (ε, 2200); $^1$H NMR (DMSO-d$_6$) δ=8.28 (s, 1H, H-8), 8.13 (s, 1H, H-2), 7.22 (br s, 2H, NH$_2$-6), 6.26 (t, 1H, H-1', J=6.7 Hz), 5.30 (br s, 1H, OH-3'), 4,19 (m, 1H, H-3'), 3.9–3.8 (m, 1H, H-4'), 2.8–2.7 (m, 1H, H-2'), 2.3–2.2 (m, 1H, H-2''), 1.24 (d, 3H, CH$_3$-5',J=6.4 Hz); $^{13}$C NMR (DMSO-d$_6$) δ=156.9 (C-6), 153.4 (C-2), 150.0 (C-4), 140.3 (C-8), 120.0 (C-5), 83.6 (C-1'), 83.2 (C4'), 75.5 (C-3'), 39.3 (CH$_2$-2'), 19.9 (CH$_{2-5}$'); MS FA>0 m/z 236 (M+H)$^+$,136 (BH$^2$)$^+$, MS FAB<0 m/z 234 (M–H)$^-$; $[α]_D^{20}$=–39 (c, 0.96, DMSO); Anal. Calcd for C$_{10}$H$_{13}$N$_5$O$_2$: C, 51.06; H, 5.57; N, 29.77.

(ii) 9-{2,5-dideoxy-3[bis(S-aryl-2-thioethyl)phosphate]-β-L-erythro-pentofuranosyl}adenine (β-L-2',5'-dd-3'-AMP-bis(acyl-SATE) (compounds 4–6). Adapting a published procedure for the synthesis of bis(t-butyl SATE) pronucleosides [50], sublimed 1H-tetrazole (61 mg, 0.88 mmol) was added to a stirred solution of 9-(2,5-dideoxy-β-L-erythro-pentofuranosyl)-adenine (β-L-2',5'-Ado; 69 mg, 0.29 mmol) in a mixture of tetrahydrofuran and dimethylformamide (1,5 ml, 2/1, v/v), followed by the dropwise addition of a solution of bis(S-2-hydroxyethylthioacyl)-N,N-diisopropylphosphoramidite (-pivaloyl-160 mg, 0.42 mmol, for compound 5) in tetrahydrofuran (0.5 ml) at room temperature. After 45 min, a 3 M solution of tert-butylhydroperoxide (0.293 ml, 0.88 mmol) in toluene was added. After further stirring at room temperature for 30 min, the mixture was diluted with dichloromethane and washed successively with 10% aqueous sodium sulfite solution and water. The organic layer was dried over sodium sulfate, filtered, and evaporated to dryness under reduced pressure. Purification of the residue by silica gel column chromatography using a stepwise gradient of 0 to 4% methanol in dichloromethane afforded 9-{2,5-dideoxy-3[bis(S-pivaloyl-2-thioethyl)phosphate]-β-L-erythro-pentofuranosyl}adenine (compound 5; 65 mg, 56%) as a colorless syrup. Syntheses of β-L-2',5'-dideoxyadenosine-3'-O-bis(S-acetyl-2-thioethyl)phosphate (compound 4) and β-L-2',5'-dideoxyadenosine-3'-O-bis(S-benzoyl-2-thioethyl)-phosphate (compound 6) follow from the respective bis(S-2-hydroxyethylthioacyl) N,N-diisopropylphosphoramidite in a similar fashion.

β-L-2',5'-dideoxyadenosine-3'-O-bis(S-pivaloyl-2-thioethyl)-phosphate (compound 5). $R_f$(MeOH/CH$_2$Cl$_2$, 10/90)=0.39; UV (EtOH 95)λmax 259 nm (ε, 14200), 236 nm (ε,10300), λmin 240 nm (ε, 10100); $^1$H NMR (CDCl3) δ=8.28 (s, 1H, H-8), 7.87 (s, 1H, H-2), 6.30 (t, 1H, H-1', J=6.8 Hz), 5.58 (br s, 2H, NH$_2$–6), 4.9-4.8 (m, 1H, H-3'), 4.3–4.2 (m, 1H, H-4'), 4.1–4.0 (m, 4H, 2'CH$_2$O), 3.2–3.0 (m, 5H, 2'CH$_2$S and H-2'), 2.7–2.6 (m, 1H, H-2''), 1.40 (d, 3H, CH$_3$-5', J=6.6 Hz), 1.17 and 1.16 (2s, 18 H, 2'(CH$_3$)$_3$C; $^{13}$C NMR (CDCl$_3$) δ=2.06.1 (2'CO), 155.8 (C-6), 153.5 (C-2), 150.1 (C-4), 139.6 (C-8), 120.9 (C-5), 84.8 (C-1'), 82.1(C-4'), 66.8 (2'CH$_2$O), 66.7 (C-3'), 47.0 (2'C(CH$_3$)$_3$), 38.1(CH$_2$-2'), 28.9 (2'CH$_2$S), 27.7 (2'(CH$_3$)$_3$), 19.6 (CH$_3$-5'); $^{31}$P NMR (CDCl$_3$) δ=–2.05; MS FAB>0 m/z 604 (M+H)$^+$, 136 (BH$^2$)$^+$, MS FAB<0 m/z 458 (M-tBuSATE)$^-$, 134 (B)$^-$ HPLC: elution with a linear gradient of 0% to 80% acetonitrile in 20 mM triethylammonium acetate buffer (pH 7) programmed over 30 min at 1 ml/min, Rt=25.8 min (99.67% area); isocratic elution with 45% acetonitrile in 20 mM triethylammonium acetate (pH 7) at 1 ml/min: Rt=13.7 min (99.70% area). HRSM Calcd for C$_{24}$H$_{39}$N$_5$O$_7$PS$_2$ (M+H)$^+$: 604.2113. Found: 604.2029.

iii) General Methods for compounds 4–6. $^1$H and $^{13}$C NMR spectra were recorded at 400 MHz with proton decoupling, at ambient temperature, with a Broker DRX400. Chemical shifts are given in δ-values referenced to the residual solvent peak: chloroform (CDCl$_3$) at 7.26 ppm and 77.6 ppm or dimethylsulfoxide (DMSO-d$_6$) at 2.49 ppm and 39.5 ppm, relative to tetramethylsilane (TMS), Coupling constants, J, are reported in Hz. Deuterium exchange, decoupling and COSY experiments were performed in order to confirm proton assignments. 2D $^1$H-$^{13}$C heteronuclear COSY were recorded for the attribution of $^{13}$C signals. $^{31}$P NMR spectra were recorded at ambient temperature at 400 MHz with proton decoupling. Chemical shifts are reported relative to external H$_3$PO$_4$. FAB mass spectra were recorded in the positive-ion and negative-ion modes on a JEOL SX 102 using thioglycerol/glycerol (1:1, v/v, G-T) as matrix. Melting points were determined in open capillary tubes on a Gallenkamp MFB-595-010M apparatus and are uncorrected. UV spectra were recorded on a Uvikon 931(Kontron) spectropolarimeter. Specific rotations were measured in a 1 cm cell on a Perkin-Elmer Model 241 spectropolarimeter settled on the sodium D line. Elemental analyses were carried out by the "Service de Microanalyses du CNRS, Division de Vernaison (France)." Thin layer chromatography was performed on precoated aluminum sheets of silica gel 60 F$_{254}$ (Merck, Art. 9885), visualization of products was accomplished by UV absorbance followed by charming with 10% ethanolic sulfuric acid with heating and/or by spraying with Hones molybdate reagent. Column chromatography was carried out on silica gel 60 (Merck, Art. 9385). HPLC analysis was carried out using a reverse-phase analytical column (Nucleosyl, C18, 150×4.6 mm, 5µm) equipped with a prefilter, a precolumn (Nacleosyl, C18, 5 µm) and a photodiode array detector (detection at 260 nm). All moisture-sensitive reactions were carried out under rigorous anhydrous conditions under argon atmosphere using oven-dried glassware. Solvents were dried and distilled prior to use and solids were dried over P$_2$O$_5$ under reduced pressure at room temperature.

EXAMPLE 2

Effects of Nucleotide Prodrugs on PH/cAMP Formation in Isolated Cells

The nucleotide prodrugs were tested for their capacity to inhibit the forskolin-stimulated formation of [$^3$H]cAMP in cells that had been preloaded with [$^3$H]adenine [47]. Human macrophages and two preadipocyte cell lines were tested.

Cell culture (i) Preadipocytes: Preadipocytes were cultured in DMEM LG medium that was supplemented with 8% fetal bovine serum and 1% of an antibiotics mixture in 2 ml Petri dishes until they reached 90–95% confluence. Growth medium was removed and 1 ml of DMEM LG medium containing 2,8-[$^3$H]-adenine (5µCi) was added to each dish. Cells were incubated for 2 h at 37° C. Medium was removed and cells were incubated for 15 min at 37° C. in 1 ml of unsupplemented medium. The medium was removed and 1 ml of DMEM LG medium supplemented with 0.1 mg/ml bovine serum albumin and 0.1 mM 3-isobutyl-1-methylxanthine was added.

(ii) Macrophages. Macrophages were plated on culture dishes and allowed to adhere in RPMI culture medium. Cells were labeled with 2,8-[$^3$H]-adenine as described above for the preadipocytes.

Experimental treatment

Ten microliters of a solution of the test substance was added to yield the appropriate concentration of inhibitor in the medium. After 15 min of incubation at 37° C. 3 µl of a 10 mM solution of forskolin in ethanol was added to the medium and the cells were further incubated for 15 min at 37° C. The medium was removed and the reaction was stopped by the addition of 1 ml of a freshly prepared solution of 0.5 mM solution of cAMP in 0.3 M perchloric acid. Dishes were then kept on ice for 30 min. To 800 µl of the resulting cell extract was then added 90 µl of 0.5 M triethanolammonium chloride butler (pH=7.5). The extract was then neutralized by addition of aqueous potassium hydroxide. [$^3$H]cAMP was purified from a 700 µl portion of this mixture by sequential chromatography on Dowex 50 and alumina as previously described [3]. A portion of the purified sample was used to quantify the [$^1$H]cAMP formed and the remainder was used to quantify recovery by UV spectroscopy.

The expectation was that the nucleotide prodrug forms of these agents would enter cells, be deprotected, and be phosphorylated to the corresponding forms with three phosphates, which would then cause a potent inhibition of adenylyl cyclase. It was additionally expected that the order of potency in intact cells would follow the potency of the phosphorylated ligands to inhibit adenylyl cyclase, that is PMEApp (IC$_{50}$ 170 nM)<2',5'-dd-3'-ATP (IC$_{50}$ 40 nM)<β-L-2',3'-dd-5'-ATP (IC$_{50}$ 24 nM) (Table 1). However, this was not the case and substantial selectivity of these nucleotide prodrugs was observed (Table 2). Moreover, with both preadipocyte cell lines 2',5'-dd-3'-AMP-bis(t-Bu-SATE) (compound 2) caused accelerated rates of differentiation (not shown), similar to effects noted earlier with the precursor nucleoside, 2',5'dd-Ado [40]. Furthermore, 2',5'-dd-3'-AMP-bis(t-Bu-SATE) (2) had no effect on the activity of adenylyl cyclases per se, whether enzyme was from rat brain or from the preadipocytes, whereas the cyclosalicyl-derivatives were weak inhibitors (Table 3). This latter weak inhibition was likely due to the spontaneous deprotection that the cyclosalicyl-derivatives undergo in aqueous solutions [5].

TABLE 2

Effects of various pro-nucleotides to inhibit forskolin-stimulated formation of [$^3$H]cAMP from cells prelabeled with [$^3$H]adenine.

| Pro-Nucleotide | Ob1771 pre-adipocytes IC$_{50}$ (nM) | F442A pre-adipocytes IC$_{50}$ (nM) | Human Macrophages IC$_{50}$ (nM) |
|---|---|---|---|
| β-D-2',5'-dd-3'-AMP-bis(Me-SATE) (1) | | 30 | |
| β-D-2',5'-dd-3'-AMP-bis(t-Bu-SATE) (2) | 30 | 100 | 50 |

TABLE 2-continued

Effects of various pro-nucleotides to inhibit forskolin-stimulated formation of [$^3$H]cAMP from cells prelabeled with [$^3$H]adenine.

| Pro-Nucleotide | Ob1771 pre-adipocytes IC$_{50}$ (nM) | F442A pre-adipocytes IC$_{50}$ (nM) | Human Macrophages IC$_{50}$ (nM) |
|---|---|---|---|
| β-D-2',5'-dd-3'-AMP-bis(Ph-SATE) (3) | | 800 | |
| β-L-2',5'-dd-3'-AMP-bis(t-Bu-SATE) (5) | | ~2000 | |
| β-L-2',3'-dd-5'-AMP-bis(t-Bu-SATE) (8) | >30000 | | |
| t-Bu-SATE-PMEA (13) | >30000 | | |
| t-Bu-SATE-PMPA (16) | | >30000 | |
| β-D-2',5'-dd-3'-AMP-HSal (10) | ~2000 | | ~2000 |
| β-D-2',5'-dd-3'-AMP-MeSal (11) | ~2000 | | |
| (1R,2S)-9-(cyclopentyl)-Ade-2'-P-bis(t-Bu-SATE) (ns) | >30000 | | |
| (1S,2R)-9-(cyclopentyl)-Ade-2'-P-bis(t-Bu-SATE) (ns) | >30000 | | |

Bold numbers in parentheses refer to compounds given on pages 11–12; (ns) indicates the compound not shown. For comparison with the values given in Table 1, IC$_{50}$ values for inhibition of rat brain adenylyl cyclase by 2'-triphosphate forms of (1'R,2'S)- and (1'S,2'R)-enantiomers of 9-(cyclopentyl)-adenine were 450 nM and 9860 nM respectively.

TABLE 3

Protected 2',5'-dd-3'-AMP does not inhibit isolated adenylyl cyclases (IC$_{50}$).

| | Rat Brain Adenylyl Cyclase | Ob1771 cell membranes |
|---|---|---|
| β-D-2',5'-dd-3'-AMP-(H-Sal) (10) | 7 µM | 30 µM |
| β-D-2',5'-dd-3'-AMP-(Me-Sal) (11) | 7 µM | 60 µM |
| β-D-2',5'-dd-3'-AMP-bis(t-Bu-SATE) (2) | no inhibition at 100 µM | 20% inhibition at 100 µM |

Adenylyl cyclase activities were determined as previously described [24–32], with a reaction mixture containing 100 µM 5'ATP, 5 mM MnCl$_2$, and 100 µM forskolin. IC$_{50}$ values were determined graphically.

The data suggest that the effectiveness of the nucleotide prodrugs in cells was not a function solely of the potency of their presumed triphosphate derivatives to inhibit adenylyl cyclases, but that efficacy may be dictated also by the processing of the prodrugs and the mechanisms by which inhibition occurs. The most effective agents were the prodrug precursors of 2',5'-dd-3'-ATP, a non-competitive, post-transition-state inhibitor. The prodrug precursors of β-L-2',3'-dd-5'-ATP and PMEA were ineffective in intact cells, despite the fact that these nucleotides were potent inhibitors of isolated adenylyl cyclase. β-L-2',3'-dd-5'-ATP is a pre-transition-state competitive inhibitor, and PMEApp causes mixed inhibition [31]. The data are fully consistent with there being a preferential structure of nucleotide prodrug which acts solely on intact cells to cause an intracellular inhibition of adenylyl cyclase and a consequential shutdown of cAMP/PKA-mediated pathways.

EXAMPLE 3

Effect of β-D-2',5'-dd-3'-AMP-bis(t-Bu-SATE) Cardiac Myocytes

The efficacy of 2',5'-dd-3'-AMP-bis(t-Bu-SATE) in isolated preadipocytes and macrophages (Table 2) suggested that it should work in other tissues as well. Cardiac ventricular myocytes exhibit an isoproterenol-stimulated, cAMP/PKA-dependent Cl⁻ channel [48]. Cl⁻ channel function was also blocked by 2',5'-dd-3'-AMP-bis(t-Bu-SATE) (($C_{50}$~82 nM) (not shown). Thus, in three cell types and with two different end-points, this prodrug showed a striking potency to block stimulated responses, whether by hormone or by an agent acting directly on adenylyl cyclase.

EXAMPLE 4

Effects of μ-D-2',5'-dd-3'-AMP-bis(t-Bu-SATE) (2) on Cardiac Function

The blockade by 2',5'-dd-3'-AMP-bis(t-Bu-SATE) (2) of isoproterenol-stimulated Cl⁻ channel activity in ventricular myocytes suggested that this pronucleotide should also affect other aspects of cardiac function. To test this, rat atria were excised from a male albino rat and attached to a strain gauge to allow contractions to be measured. The spontaneously contracting tissue was suspended in a chamber and allowed to equilibrate for 15 min in Krebs-Henseleit medium (Sigma K3753) supplemented with 25 mM $NaHC_3$, 2.5 mM $CaCl_2$, and 2 mM pyruvate, maintained at 37° and continuously gassed with 9%/5% $CO_2$. The stimulation of contractility caused by phenylephrine or forskolin (not shown) were completely blocked by preincubation with 10 μM 2',5'-dd-3'-AMP-bis(t-Bu-SATE) for 15 min.

From the above examples it is likely that 2',5'-dd-3'-AMP-bis(t-Bu-SATE) will act in many cells and tissues to block regulation that is mediated by the cAMP/PKA pathway. Potencies and efficacies may differ from those noted here (Table 2) and this may be attributable to differences in expression levels and sensitivities of the various adenylyl cyclase isozymes. The expectation is that 2',5'-dd-3'-AMP-bis(t-Bu-SATE), 2',5'-dd-3'-AMP-bis(Me-SATE), 2',5'-dd-3'-AMP-bis(Ph-SATE), and other nucleotide prodrugs that are similarly based on adenine nucleoside 3'-phosphates, but with different protecting groups, will constitute a family of agents that can be used to inhibit adenylyl cyclases in intact cells and tissues. It is important to note that 2',5'-dd-3'-AMP-bis(t-Bu-SATE), even at concentrations up to 300 μM had no effect on adenylyl cyclase isolated from these tissues, i.e., effects of this nucleotide prodrug were elicited only in the intact cell. The expected selectivity of this group will be due to both the general potency of adenine nucleoside 3'-polyphosphates to inhibit adenylyl cyclases and to the fact that this group of ligands inhibit adenylyl cyclases by a noncompetitive, post-transition state mechanism.

The 9-substituted adenine derivatives of the invention may include other rationally designed structures including, for example, equivalent of 3'-phosphate or 3'-thiophosphate derivatives that are protected by groups that allow the resulting 3'-phosphate- or 3'-thiophosphate-containing ligand to enter cells and tissues. Although the emphasis here has been with derivatives of -S-acyl-2-thioethyl (SATE) as protecting groups, other protecting groups are also to be included. These include, for example, -H(salicyl) and -methyl(salicyl) groups, amino acids coupled through hydroxyl- or thio- groups, N-coupled amino acids, amines, sugars, amino sugars, lipids, fatty acids, glycols, nucleotides, nucleosides, fluorophores [34, 52], steroids (e.g., cholesteryl groups [34, 52]), dithioethyl derivatives [55], and derivatives of these. Many of these compounds will become useful and valuable agents for pharmacological and biochemical investigations involving intact cells, tissues, and organisms.

REFERENCES

1) Taylor, S. (1989) *J. Biol. Chem.* 264: 8443–8446.
2) Francis, S. H., and Corbin J. D. (1999) *Crit. Rev. Clin. Lab. Sci.* 36(4): 275–328.
3) Zagotta, W. N., and Siegelbaum, S. A. (1996) *Ann. Rev. Neurosciences* 19: 235–263.
4) Finn, J. T., Grunwald, M. E., and Yau, K. W. (1996) *Ann. Rev. Physiol.* 58: 395–426.
5) Sutherland, E. W., Rall, T. W., and Meson, T. (1962) *J. Biol. Chem.* 237:1220–1227.
6) Smit, M. J., and Iyengar, R. (1998) *Adv. Second Messenger & Phosphoprotein Res.* 32: 1–21.
7) Butcher, R. W., and Sutherland, E. W. (1962) *J. Biol. Chem.* 237:1244–1250.
8) Beavo, J. A. (1995) *Physiological Rev.* 75: 725–748.
9) Rodbell, M., Bimbaumer, L., Pohl, S. L., and Krans, H. M. J. (1971) *J. Biol. Chem.* 246:1877–1882.
10) Rodbell, M. (1995) *Angew. Chem. Int. Ed. Engl.* 34:1420–1428.
11) Gilman, A. G. (1995) *Angew. Chem. Int. Ed. Engl.* 34: 1406–1419.
12) Brostrom, C. O., Huang, Y., Breckenridge, B. M., and Woolf. D. J. (1975) *Proc. Natl. Acad. Sci. USA* 72: 64–68.
13) Seamon, K. and Daly, J. W. (1981) *J. Biol. Chem.* 256: 9799–9801.
14) De Souza, N. J. (1993) *J. Ethnopharmacol.* 38: 177.
15) Drummond, G. I. (1981) *Arch. Biochem. Biophys.* 211: 30–38.
16) Moullet, O., and Dreyer, J. -L. N(1994) *Biochem. J.* 300: 99–106.
17) Yoshimasa, T., Sibley, D. R., Bouvier, M., Lefkowitz, R. J., Caron, M. G. (1987) *Nature* 327:67–70.
18) Weinryb, I., and Michel, I. M. (1974) *Biochem. Biophys. Acta* 334: 218–225.
19) Londos, C., and Wolff, J. (1977) *Proc. Natl. Acad. Sci. USA* 74: 5482–5486.
20) Haslam, R. J., Davidson, M. M. L., and Desjardins, J. V. (1978) *Biochem. J.* 176:83–95.
21) Johnson, R. A., Saur, W. and Jakobs, K. H. (1979) *J. Biol. Chem.* 254: 1094–1101.
22) Londos, C., Cooper, D. M. F., and Wolff, J. (1980) *Proc. Natl. Acad. Sci. USA* 77:1551–2554.
23) Florio, V. A., and Ross, E. M. (1983) *Molec. Pharmacol* 24:195–202.
24) Johnson, R. A. Young, S. M. H., Stübner, D., Bushfield, M., and Shoshani, I. (1989) *Mol. Pharmacol.* 35: 681–688.
25) Bushfield, M., Shoshani, I., and Johnson, R. A. (1990) *Molec, Pharmacol.* 38; 848–853.
26) Johnson, R. A., and Shoshani, I. (1990) *J. Biol. Chem.* 265:11595–11600.
27) Young, S. -M. H., and Johnson, R. A. (1990) *J. Biol. Chem.* 265: 16745–16750.
28) Désaubry, L, Shoshani, I, and Johnson, R. A, (1996) *J. Biol. Chem.* 271: 2380–2383.
29) Désaubry, L., Shoshani, I., and Johnson, R. A. (1996) *J. Biol. Chem.* 271: 14028–14034.
30) Désaubry, L, and Johnson, R. A. (1998) *J. Biol. Chem.* 38: 24972–24977.

31) Shoshani, I., Boudou, V., Pierra, C., Gosselin, G., and Johnson, R. A. (1999) *J. Biol. Chem.* 274:34735–34741.
32) Shoshani, I., Laux, W. H. G., Périgaud, C., Gosselin, G., and Johnson, R. A. (1999) *J. Biol. Chem.* 274: 34742–34744.
33) Dessauer, C. W., and Gilman, A. G. (1997) *J. Biol. Chem.* 272: 27787–27795.
34) Johnson, R. A., Désaubry, L., and Shoshani, I, (1998) "Method and compounds for the inhibition of adenylyl cyclase. U.S. Pat. No. 5,795,756.
35) Johnson, R. A., Désaubry, L., and Shoshani, I. (2000) U.S. patent application Ser. No. 09/071,779.
36) Tesmer, J. J. G., Sunahara, R. K., Johnson, R. A., Gosselin, G., Gilman, A. G., and Sprang, S. R. (1999) *Science* 285: 756–760.
37) Tesmer, J. J. G., Déssauer, C. W., Sunahara, R. K., Murray, L. D., Johnson, R. A., Gilman, A. G., and Sprang, S. R. (2000) *J. Biol. Chem.* 275: (In review).
38) Fain, J. N., Pointer, R. H., and Ward, W. F. (1972) *J. Biol. Chem.* 247: 6866–6872.
39) Claus, T. H., Anand-Srivastava, M. B., and Johnson, R. A.(1982) *Molec. & Cell Endocrinol.* 26: 269–279.
40) Ibrahimi, A., Abumrad, N., Maghareie, H., Golia, M., Shoshani, I., Désaubry, L., and Johnson, R. A. (1999) *Am J. Physiol.* 276 (*Cell Physiol.* 45); C487–C496.
41) Gärtner, R., Greil, W., Demharter, R., and Horn, K. (1985) *Molec. Cell. Endocrin.* 42: 145–155.
42) Grega, D. S., and Macdonald, R. L. (1987) *J. Neuroscience* 7(3): 700–707.
43) Reid, I.R., Lowe, C., Cornish, J., Grayh, D. H., and Skinner, S. J. M. (1990) *Am. J. Physiol.* 258 (Endocrinol. Metab. 21): E708–E714.
44) Dillingham, M. A., and Anderson, R. J. (1985) *J. Membrane Biol.* 88: 277–281.
45) Thomas, C. A., Weinberger, O. K., Ziegler, B. L, Greenberg, S., Schieren, I., Silverstein, S. C., and Khoury, J. E. (1997) *Blood* 90: 3760–3765.
46) Benzaria, S., Pelicano, H, Johnson, R., Maury, G., Imbach, J. L, Aubertin, A. -M., Obert, G., and Gosselin, G. (1996) *J. Med. Chem.* 39: 4958–4965.
47) Salomon Y. (1991) *Methods Enzymol.* 195:22–28.
48) Hiraoka, M., Kawano, S., Hirano, Y., and Furukawa, T. (1998) *Cardiovascular Res.* 40: 23–33.
49) Hoffman, B. B., and Lefkowitz, R. J., In: *The Pharmacological Basis of Therapeutics*, (Hardman, Limbird, Molinoff, Ruddon, and Gilman, Eds.) 9$^{th}$ Edition, pp. 199–248, McGraw-Hill, New York, 1996.
50) Lefebvre, I., Perigaud, C., Pompon, A., Aubertin, A. -M., Girardet, J. -L., Kim, A., Gosselin, G., and Imbach, J. -L. (1995) *J. Med. Chem.*, 38: 3941–3950.
51) Meier, C. (1996) *Angew. Chem. Int. Ed. Engl.* 35: 70–72.
52) Désaubry, L., Shoshani, I., Johnson, R. A. (1995) *Nucleosides & Nucleotides* 14: 1453–1460.
53) Holy, A., and Masojidkova, M. (1995) *Collect. Czech. Chem. Commun.* 60: 1196–1212.
54) Holy, A., and Rosenberg, I. (1987) *Collect. Czech. Chem. Commun.* 52: 2801–2809.
55) Perigaud, C., Gosselin, G., Lefebvre, I, Girardet, J. -L, Benzaria, S., Barber, I., Imbach, J. -L. (1993) *Bioorg. Med. Chem. Lett.* 3:2521–2526.

What is claimed is:

1. A compound represented by formula (I)

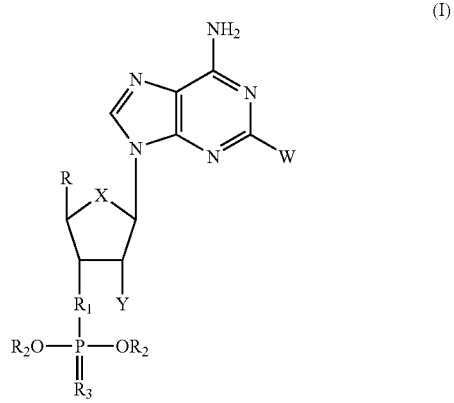

wherein W is selected from the group consisting of H, halogen, azido and amino group;

X is selected from the group consisting of O, S, N(H), $CH_2$ and CH;

Y is selected from the group consisting of H, hydroxy, $C_{1-4}$ alkyl, $C_{1-4}$ alkoxy and halogen;

R is selected from the group consisting of H, hydroxymethyl, $C_{1-4}$ alkyl, and $C_{1-4}$ alkoxy;

$R_1$ is selected from the group consisting of O, NH and $CH_2$;

$R_2$ represents a radical selected from the group consisting of —$(CH_2)_n$—S—C(O)—$R_4$ and —$(CH_2)_n$—S—S—$R_4$, where n=1–4 and $R_4$ is a $C_{1-4}$ alkyl or aryl group and $R_4$ is optionally substituted with a halogen, amino, N-alkylamino, N,N-dialkylamino or $C_{1-4}$ alkoxy group and wherein each of the $R_2$ radicals may be the same or different;

$R_3$ is O or S; and when X is CH the ring so formed is unsaturated and when X is $CH_2$ the ring so formed is saturated.

2. The compound of claim 1 where W is a hydrogen atom, and $R_2$ represents a radical selected from the group consisting of —$CH_2$—$CH_2$—S—C(O)—$R_4$ and —$CH_2$—$CH_2$—S—S—$R_4$, where $R_4$ is a $C_{1-4}$ alkyl or aryl group.

3. The compound of claim 2 where $R_4$ is a radical selected from the group consisting of methyl, tent-butyl and phenyl.

4. The compound of claim 1 where R is selected from the group consisting of H, hydroxymethyl, methyl and methoxy.

5. The compound of claim 1 where Y is selected from the group consisting of H, hydroxymethyl and methoxy.

6. The compound of claim 1 wherein X is O, Y is hydroxy, R is hydroxymethyl and $R_1$ is O.

7. The compound of claim 1 where X is S.

8. The compound of claim 1 where X is N(H).

9. The compound of claim 1 where X is $CH_2$.

10. A compound selected from the group consisting of:
2',5'-dideoxy-β-(L)-adenosine 3'-bis(S-acetyl-2-thioethyl)-monophosphate;
2',5'-dideoxy-β-(D)-adenosine 3'-bis(S-acetyl-2-thioethyl)-monophosphate;
2'-deoxy-β-(L)-adenosine 3'-bis(S-acetyl-2-thioethyl)-monophosphate;
2'-deoxy-β-(D)-adenosine 3'-bis(S-acetyl-2-thioethyl)-monophosphate;
2',5'-dideoxy-β-(L)-adenosine 3'-bis(S-pivaloyl-2-thioethyl)-monophosphate;

2',5'-dideoxy-β-(D)-adenosine 3'-bis(S-pivaloyl-2-thioethyl)-monophosphate;
2'-deoxy-β-(L)-adenosine 3'-bis(S-pivaloyl-2-thioethyl)-monophosphate;
2'-deoxy-β-(D)-adenosine 3'-bis(S-pivaloyl-2-thioethyl)-monophosphate;
2',5'-dideoxy-β-(L)-adenosine 3'-bis(S-benzoyl-2-thioethyl)-monophosphate;
2',5'-dideoxy-β-(D)-adenosine 3'-bis(S-benzoyl-2-thioethyl)-monophosphate;
2'-deoxy-β-(L)-adenosine 3'-bis(S-benzoyl-2-thioethyl)-monophosphate;
2'-deoxy-β-(D)-adenosine 3'-bis(S-benzoyl-2-thioethyl)-monophosphate;
2',5'-dideoxy-β-(L)-adenosine 3'-deoxy-3'-bis(S-acetyl-2-thioethyl)-methylenephosphonate;
2',5'-dideoxy-β-(D)-adenosine 3'-deoxy-3'-bis(S-acetyl-2-thioethyl)-methylenephosphonate;
2'-deoxy-β-(L)-adenosine 3'-deoxy-3'-bis(S-acetyl-2-thioethyl)-methylenephosphonate;
2'-deoxy-β-(D)-adenosine 3'-deoxy-3'-bis(S-acetyl-2-thioethyl)-methylenephosphonate;
2',5'-dideoxy-β-(L)-adenosine 3'-deoxy-3'-bis(S-pivaloyl-2-thioethyl)-methylenephosphonate;
2',5'-dideoxy-β-(D)-adenosine 3'-deoxy-3'-bis(S-pivaloyl-2-thioethyl)-methylenephosphonate;
2'-deoxy-β-(L)-adenosine 3'-deoxy-3'-bis(S-pivaloyl-2-thioethyl)-methylenephosphonate;
2'-deoxy-β-(D)-adenosine 3'-deoxy-3'-bis(S-pivaloyl-2-thioethyl)-methylenephosphonate;
2',5'-dideoxy-β-(L)-adenosine 3'-deoxy-3'-bis(S-benzoyl-2-thioethyl)-methylenephosphonate;
2',5'-dideoxy-β-(D)-adenosine 3'-deoxy-3'-bis(S-benzoyl-2-thioethyl)-methylenephosphonate;
2'-deoxy-β-(L)-adenosine 3'-deoxy-3'-bis(S-benzoyl-2-thioethyl)-methylenephosphonate;
2'-deoxy-β-(D)-adenosine 3'-deoxy-3'-bis(S-benzoyl-2-thioethyl)-methylenephosphonate;
2',5'-dideoxy-β-(L)-adenosine 3'-deoxy-3'-bis(S-acetyl-2-thioethyl)-N-phosphoramidate;
2',5'-dideoxy-β-(D)-adenosine 3'-deoxy-3'-bis(S-acetyl-2-thioethyl)-N-phosphoramidate;
2'-deoxy-β-(L)-adenosine 3'-deoxy-3'-bis(S-acetyl-2-thioethyl)-N-phosphoramidate;
2'-deoxy-β-(D)-adenosine 3'-deoxy-3'-bis(S-acetyl-2-thioethyl)-N-phosphoramidate;
2',5'-dideoxy-β-(L)-adenosine 3'-deoxy-3'-bis(S-pivaloyl-2-thioethyl)-N-phosphoramidate;
2',5'-dideoxy-β-(D)-adenosine 3'-deoxy-3'-bis(S-pivaloyl-2-thioethyl)-N-phosphoramidate;
2'-deoxy-β-(L)-adenosine 3'-deoxy-3'-bis(S-pivaloyl-2-thioethyl)-N-phosphoramidate;
2'-deoxy-β-(D)-adenosine 3'-deoxy-3'-bis(S-pivaloyl-2-thioethyl)-N-phosphoramidate;
2',5'-dideoxy-β-(L)-adenosine 3'-deoxy-3'-bis(S-benzoyl-2-thioethyl)-N-phosphoramidate;
2',5'-dideoxy-β-(D)-adenosine 3'-deoxy-3'-bis(S-benzoyl-2-thioethyl)-N-phosphoramidate;
2'deoxy-β-(L)-adenosine 3'-deoxy-3'-bis(S-benzoyl-2-thioethyl)-N-phosphoramidate; and
2'-deoxy-β-(D)-adenosine 3'-deoxy-3'-bis(S-benzoyl-2-thioethyl)-N-phosphoramidate.

11. A compound selected from the group consisting of:
9-(tetrahydrofuryl)-(1'R,3'S)-adenine-3'-bis(S-acetyl-2-thioethyl)-monophosphate;
9-(tetrahydrofuryl)-(1'R,3'R)-adenine-3'-bis(S-acetyl-2-thioethyl)-monophosphate;
9-(tetrahydrofuryl)-(1'R,3'S)-adenine-3'-bis(S-pivaloyl-2-thioethyl)-monophosphate;
9-(tetrahydrofuryl)-(1'R,3'R)-adenine-3'-bis(S-pivaloyl-2-thioethyl)-monophosphate;
9-(tetrahydrofuryl)-(1'R,3'S)-adenine-3'-bis(S-benzoyl-2-thioethyl)-monophosphate;
9-(tetrahydrofuryl)-(1'R,3'R)-adenine-3'-bis(S-benzoyl-2-thioethyl)-monophosphate;
9-(tetrahydrofuryl)-(1'R,3'S)-adenine-3'-deoxy-3'-bis(S-acetyl-2-thioethyl)-methylenephosphonate;
9-(tetrahydrofuryl)-(1'R,3'R)-adenine-3'-deoxy-3'-bis(S-acetyl-2-thioethyl)-methylenephosphonate;
9-(tetrahydrofuryl)-(1'R,3'S)-adenine-3'-deoxy-3'-bis(S-pivaloyl-2-thioethyl)-methylenephosphonate;
9-(tetrahydrofuryl)-(1'R,3'R)-adenine-3'-deoxy-3'-bis(S-pivaloyl-2-thioethyl-methylenephosphonate;
9-(tetrahydrofuryl)-(1'R,3'S)-adenine-3'-deoxy-3'-bis(S-benzoyl-2-thioethyl)-methylenephosphonate;
9-(tetrahydrofuryl)-(1'R,3'R)-adenine-3'-deoxy-3'-bis(S-benzoyl-2-thioethyl)-methylenephosphonate;
9-(tetrahydrofuryl)-(1'R,3'S)-adenine-3'-deoxy-3'-bis(S-acetyl-2-thioethyl)-N-phosphoramidate;
9-(tetrahydrofuryl)-(1'R,3'R)-adenine-3'-deoxy-3'-bis(S-acetyl-2-thioethyl)-N-phosphoramidate;
9-(tetrahydrofuryl)-(1'R,3'S)-adenine-3'-deoxy-3'-bis(S-pivaloyl-2-thioethyl)-N-phosphoramidate
9-(tetrahydrofuryl)-(1'R,3'R)-adenine-3'-deoxy-3'-bis(S-pivaloyl)-2-thioethyl)-N-phosphoramidate
9-(tetrahydrofuryl)-(1'R,3'S)-adenine-3'-deoxy-3'-bis(S-benzoyl-2-thioethyl)-N-phosphoramidate; and
9-(tetrahydrofuryl)-(1'R,3'R)-adenine-3'-deoxy-3'-bis(S-benzoyl-2-thioethyl)-N-phosphoramidate.

12. A compound selected from the group consisting of:
9-(cyclopentyl)-(1'R,3'S)-adenine-3'-bis(S-acetyl-2-thioethyl)-monophosphate;
9-(cyclopentyl)-(1'R,3'R)-adenine-3'-bis(S-acetyl-2-thioethyl)-monophosphate;
9-(cyclopentyl)-(1'R,3'S)-adenine-3'-bis(S-pivaloyl-2-thioethyl)-monophosphate;
9-(cyclopentyl)-(1'R,3'R)-adenine-3'-bis(S-pivaloyl-2-thioethyl)-monophosphate;
9-(cyclopentyl)-(1'R,3'S)-adenine-3'-bis(S-benzoyl-2-thioethyl)-monophosphate;
9-(cyclopentyl)-(1'R,3'R)-adenine-3'-bis(S-benzoyl-2-thioethyl)-monophosphate;
9-(cyclopentyl)-(1'R,3'S)-adenine-3'-deoxy-3'-bis(S-acetyl-2-thioethyl)-methylenephosphonate;
9-(cyclopentyl)-(1'R,3'R)-adenine-3'-deoxy-3'-bis(S-acetyl-2-thioethyl)-methylenephosphonate;
9-(cyclopentyl)-(1'R,3'S)-adenine-3'-deoxy-3'-bis(S-pivaloyl-2-thioethyl)-methylenephosphonate;
9-(cyclopentyl)-(1'R,3'R)-adenine-3'-deoxy-3'-bis(S-pivaloyl-2-thioethyl)-methylenephosphonate;
9-(cyclopentyl)-(1'R,3'S)-adenine-3'-deoxy-3'-bis(S-benzoyl-2-thioethyl)-methylenephosphonate;
9-(cyclopentyl)-(1'R,3'R)-adenine-3'-deoxy-3'-bis(S-benzoyl-2-thioethyl)-methylenephosphonate;

9-(cyclopentyl)-(1'R,3'S)-adenine-3'-deoxy-3'-bis(S-acetyl-2-thioethyl)-N-phosphoramidate;

9-(cyclopentyl)-(1'R,3'R)adenine-3'-deoxy-3'-bis(S-acetyl-2-thioethyl)-N-phosphoramidate;

9-(cyclopentyl)-(1'R,3'S)-adenine-3'-deoxy-3'-bis(S-pivaloyl-2-thioethyl)-N-phosphoramidate;

9-(cyclopentyl)-(1'R,3'R)-adenine-3'-deoxy-3'-bis(S-benzoyl-2-thioethyl)-N-phosphoramidate;

9-(cyclopentyl)-(1'R,3'S)-adenine-3'-deoxy-3'-bis(S-benzoyl-2-thioethyl)-N-phosphoramidate; and 9-(cyclopentyl)-(1'R,3'R)-adenine-3'-deoxy-3'-bis(S-benzoyl-2-thioethyl)-N-phosphoramidate.

13. A composition comprising a compound of claim 1 and an acceptable excipient.

14. A method for reducing adenylyl cyclase activity in intact cells and tissues comprising:
   a) selecting a compound from claim 1; and
   b) contacting the compound with cells or tissues that contain adenylyl cyclase for a period of time and under such conditions such that the adenylyl cyclase activity is reduced.

15. The method of claim 14 further comprising assessing the reduction of adenylyl cyclase activity by assay for 3':5'-cAMP.

16. The method of claim 15 wherein the assay for 3':5'-cAMP is a biochemical means of measuring tissue levels of 3':5'-cAMP selected from the group consisting of protein kinase binding assays, radioimmunoassays, ELISA and fluorometric assays.

17. The method of claim 15 wherein the assay for 3':5'-cAMP is selected from the group consisting of measuring the formation of 3':5'-cAMP in cells prelabeled with adenine and contacting intact cells with a fluorescent indicator that responds to changes in cell 3':5'-cAMP levels.

18. A method for reducing adenylyl cyclase activity in intact cells and tissues comprising:
   a) selecting a compound from claim 10; and
   b) contacting the compound with cells or tissues that contain adenylyl cyclase for a period of time and under such conditions such that the adenylyl cyclase activity is reduced.

19. A method for reducing adenylyl cyclase activity in intact cells and tissues comprising:
   a) selecting a compound from claim 11; and
   b) contacting the compound with cells or tissues that contain adenylyl cyclase for a period of time and under such conditions such that the adenylyl cyclase activity is reduced.

20. A method for reducing adenylyl cyclase activity in intact cells and tissues comprising:
   a) selecting a compound from claim 12; and
   b) contacting the compound with cells or tissues that contain adenylyl cyclase for a period of time and under such conditions such that the adenylyl cyclase activity is reduced.

* * * * *